(12) United States Patent
Mentink et al.

(10) Patent No.: US 7,781,578 B2
(45) Date of Patent: Aug. 24, 2010

(54) POWDERED OR GRANULAR COMPOSITION BASED ON LEGUMINOUS STARCH AND USE THEREOF IN NON-FOOD AND NON-PHARMACEUTICAL APPLICATIONS

(75) Inventors: Léon Mentink, Roubaix (FR); Joël Bernaerts, Labeuvriere (FR); Jean-Pierre Graux, Lillers (FR)

(73) Assignee: Roquette Freres, Lestrem (FR)

( * ) Notice: Subject to any disclaimer, the term of this patent is extended or adjusted under 35 U.S.C. 154(b) by 800 days.

(21) Appl. No.: 10/568,406

(22) PCT Filed: Aug. 10, 2004

(86) PCT No.: PCT/FR2004/002116
§ 371 (c)(1), (2), (4) Date: Feb. 14, 2006

(87) PCT Pub. No.: WO2005/021636
PCT Pub. Date: Mar. 10, 2005

(65) Prior Publication Data
US 2006/0229207 A1 Oct. 12, 2006

(30) Foreign Application Priority Data
Aug. 26, 2003 (FR) .................... 03 10181

(51) Int. Cl.
*C08B 35/00* (2006.01)
(52) U.S. Cl. ...................................... 536/102
(58) Field of Classification Search .................. 536/102
See application file for complete search history.

(56) References Cited

U.S. PATENT DOCUMENTS

| 3,615,751 | A | 10/1971 | Lecha et al. |
|---|---|---|---|
| 3,996,061 | A | 12/1976 | Johnson |
| 4,942,191 | A | 7/1990 | Rogers |
| 5,830,884 | A | 11/1998 | Kasica et al. |
| 6,248,706 | B1 | 6/2001 | Hermann et al. |
| 2001/0003619 | A1 | 6/2001 | Lefevre et al. |
| 2003/0017959 | A1 | 1/2003 | Baeck et al. |

FOREIGN PATENT DOCUMENTS

| DE | 196 19 221 | 11/1997 |
|---|---|---|
| EP | 0 620 121 | 10/1994 |
| EP | 1 106 646 | 6/2001 |
| FR | 2 001 897 | 10/1969 |
| FR | 2 832 721 | 5/2003 |
| WO | WO 00/35413 | 6/2000 |

OTHER PUBLICATIONS

Han et al, "Characterization of Pea Starches in the Presence of Alkali and Borax", Starch/Starke, vol. 55 (2003_, pp. 457-463.*

* cited by examiner

*Primary Examiner*—Elli Peselev
(74) *Attorney, Agent, or Firm*—Young & Thompson

(57) ABSTRACT

The invention concerns a powdered or granular composition, useful for preparing non-food and non-pharmaceutical products, characterized in that it contains at least one legume starch, and at least one additive selected from a flow agent, a filler, a polymer, an active principle or a mixture thereof. The invention also concerns the use of such a composition in the non-food and non-pharmaceutical fields.

23 Claims, No Drawings

POWDERED OR GRANULAR COMPOSITION BASED ON LEGUMINOUS STARCH AND USE THEREOF IN NON-FOOD AND NON-PHARMACEUTICAL APPLICATIONS

This application is a 371 of PCT/FR04/02116, filed Aug. 20, 2004.

The present invention relates to a novel powdered or granular composition based on legume starch, which is particularly suitable for preparing products for non-food and non-pharmaceutical use, such as for instance detergents, adhesives, absorbent powders, plant-protection powders, building materials, plastics or textiles, etc.

The invention is also directed toward the use of a legume starch for the purpose of preparing such products, according to a process including at least one step of physical mixing or granulation.

Finally, the invention relates to the use of legume starch to provide a novel multifunctional composition that is useful, for example, as an absorbent, disintegrant, binder, adhesive, odor absorbent and/or active-principle support, which is useful for preparing such products.

For the purposes of the present invention, the term "powdered or granular composition" in particular means any intermediate or final composition, especially irrespective of the origin, nature, constituents, functionality(ies) and intended use(s) thereof, which is in the form of particles or granules of any granulometry, which generally flows freely and is obtained according to a process containing at least one step of physical mixing or at least one step of granulation, especially wet granulation, wherein said step is moreover possibly preceded or followed by at least one step selected in particular from the group comprising hydration, drying, compacting, pelletization, densification, grinding, screening, spheronization, coating, film-coating and hard-coating treatments.

The term "wet granulation" means any known granulation technique performed in the presence of water, steam and/or any other liquid, liquefied or molten phase. These techniques conventionally involve a step of physical mixing of the various constituents of the composition to be granulated, performed at moderate temperature, i.e. generally between 15 and 40° C. and in particular at room temperature, and at sparingly elevated pressure, generally at atmospheric pressure.

They may especially be performed on devices of mixer, granulator, mixer-granulator spheronizer, granulator-spheronizer, fluidized-bed or fluidized-drum granulator or granulator-coating types, such as those marketed by the companies Glatt, Lodige, List, Hosokawa, Shugi, Nara Machinery, Frewitt, Forberg, Kaltenbach-Thuring, APV or Romaco.

These techniques generally produce products having particles with a mean diameter of greater than 100 microns and usually of greater than 200 microns, by measurement on a laser scattering granulometer, for example of LS230 type from Beckman Coulter®, in dry mode.

For the purposes of the present invention, the term "legume" refers to any plant belonging to the cesalpiniacea, mimosacea or papilionacea families and especially any plant belonging to the papilionacea family, for instance pea, bean, broad bean, horse bean, lentil, alfalfa, clover and lupin.

This definition especially includes all the plants described in any of the tables contained in the article by Hoover et al. entitled "Composition, Structure, functionality and Chemical modification of legume starches: a review".

Preferably, the legume is selected from the group comprising pea, bean, broad bean and horse bean.

Advantageously, it is pea, the term "pea" being considered herein in its broadest accepted sense and including in particular:

all the wild varieties of "smooth pea", and all the mutant varieties of pea, irrespective of the uses for which said varieties are generally intended (human food, animal nutrition and/or other uses).

Said mutant varieties are especially those known as "mutants rug, 4" and "mutants rug 5" as described in the article by C-L Hedley et al. entitled "Developing novel pea starches", Proceedings of the Symposium of the Industrial Biochemistry and Biotechnology Group of the Biochemical Society, 1996, pp 77-87.

According to another advantageous variant, the legume is a plant, for example a variety of pea or horse bean, which gives seeds containing at least 25 weight % (dry/dry) of starch.

The term "legume starch" means any composition extracted, in any manner, from a legume and especially from a papilionacea plant, and whose starch content is greater than 90%, preferably greater than 95%, these percentages being expressed as dry weight relative to the dry weight of the composition which said legume starch constitutes.

Advantageously, this starch content is at least equal to 98% (dry/dry).

The protein content of said legume starch is less than 5%, preferably less than 2%, these percentages also being expressed as dry weight relative to the dry weight of the composition which said legume starch constitutes.

Advantageously, this protein content is not more than 1% (dry/dry), preferably not more than 0.5%. It may, for example, be of between 0.25% and 0.45%.

For the purposes of the present invention, the "legume starch" may moreover contain, generally in a total content of less than 5% (dry/dry), various constituents other than starch and proteins, in particular fats, colloidal substances, fibers, mineral elements, etc.

The amylose content of the starch contained in said composition is within a broad range, i.e. greater than 20% and less than 60%, these percentages being expressed as dry weight relative to the dry weight of starch contained in said composition.

According to a first variant, this amylose content is between 22% and 55% (dry/dry). It may advantageously be between 33% and 45% dry/dry.

Use is commonly made of mixtures of additives in particulate form for the preparation of liquid or solid finished products, for non-food or non-pharmaceutical use.

Each of these additives may have a single functionality, which is at the very least fundamental, or a plurality of functionalities with regard to the conditions for preparation, the conditions for use and the desired properties of the finished product.

By way of illustration, it has been proposed to prepare, according to a process possibly including a granulation step and especially wet granulation, particulate additives for detergent compositions, the primarily desired functionality of which was to act:

as a zeolite-based builder or cobuilder as described, for example, in patents EP 455 522 and EP 511 018 in the name of the Applicant, as a disintegrant, as described, for example, in patents WO 98/40462, WO 99/64555, CA 2 317 030 or DE 199 530 27, as a support agent for surfactants or for an antifoam agent, as described, for example, in patents EP 496 510, CA 2 300 638, CA 2 316 591 or WO 01/34756, as a support agent for bleaching activators, as described, for example, in U.S. Pat. No. 4,372,868, U.S. Pat. No. 4,695,397 and U.S. Pat. No. 5,433,881, as a support agent for fragrances, as described, for example, in patent WO 99/45091.

In all cases, it is desired for the particulate additive, possibly obtained via wet granulation, to generally simultaneously have:

a) good flowability with regard to the storage, transportation, metering and possible mixing operations leading to the finished product, b) a granulometry that is high enough to be suitable for said operations and also to limit the risks of explosability or of inhalation of dust, c) good abrasion resistance during said operations and in particular a low propensity to generate fine particles, for reasons of safety and production efficiency, d) a density that is suited to said operations and if possible to the new constraints associated with environmental protection aimed at densification of finished products in order to limit the volume of packaging and the cost of transportation, e) an ability to be dispersed and/or solubilized homogeneously and, if possible, monitored in the finished product and then in the application medium, including 1) in water or in an adhesive of sparingly elevated temperature, or 2) at the surface of a soil or a plant, f) good compressibility when said additive is incorporated, possibly as a mixture with other particulate additives, into a final composition that is to be compacted or compressed, g) good ability to act as a vector agent, especially with absorbent, dispersant and/or protective properties, for any active principle it contains, h) very good biodegradability, especially with regard to the ever more restrictive regulations related to environmental protection, i) a high degree of whiteness as desired, for example, by the manufacturers of detergent compositions or alkaline adhesives and, upstream of these, by the additive suppliers thereof, all of these industrialists generally seeking a high degree of whiteness for these finished or semifinished products, and j) the lowest possible cost price.

In addition, in the case of finished products for non-food or non-pharmaceutical use, such as detergents, adhesives, absorbent powders for printing, compositions for construction materials, compositions for plastics or textiles, plant-protection products or fertilizers, it is often desired that the additives used for the preparation of said finished products and also said finished products should be able to be used efficiently under alkaline conditions and especially in application media with a pH of between 7 and 13 approximately and most particularly between pH 8 and 11 approximately. In certain cases, on the other hand, it is required that this efficacy should be expressed in a (very) low pH range. This is the case, for example, for the scale-preventing tablets with a pH of from 1 to 5 as described in patent WO 01/62886.

It results therefrom that the components of said additives, irrespective of their nature and functionality(ies), should also be suited to such pH conditions and should especially allow the additive and the finished product containing it to have or to preserve the desired characteristics in terms of efficacy, abrasion resistance and hardness, solubility and dispersibility in water, biodegradability, color, etc.

It is known that the alkaline products contained in washing compositions especially have the effect of increasing the color, the degradation and the sensitivity to hydrolysis of active principles such as fragrances or bleaching activators, but also of the supports for these active principles, for instance starches. Accordingly, it has been recommended in U.S. Pat. No. 4,695,397 to prepare detergent additive particles in the absence of water or of liquid phase, by simply compacting and then grinding a physical mixture combining the bleaching activator, corn starch and sodium tripolyphosphate.

It is also known that the pH conditions have a very broad influence on the properties, for example in terms of swelling, solubility, gelling, dispersibility and reactivity in water, of polymeric products of natural or synthetic origin conventionally used in the preparation of compositions for non-food and non-pharmaceutical use.

Granular starches are most particularly sensitive to alkaline pH values, which significantly increase their, solubility, viscosity and color especially in aqueous medium.

Under these conditions, the starches generally cannot swell on contact with water without developing strong tackiness. This tackiness is particularly unfavorable when a starch is used in systems that need, for example, to promote in aqueous medium the dispersion of active principles and/or the disintegration of tablets and bars. In addition, the significant presence of reducing sugars in many starch derivatives is liable, in alkaline medium, to generate coloration problems in any composition containing such derivatives.

Conversely, under acidic pH conditions, starches readily undergo hydrolysis generating reducing sugars and small molecules, which has the effect of increasing the hygroscopicity and of reducing the binding power of the resulting starchy composition.

These abovementioned drawbacks, associated with the use of starches and derivatives in media having alkaline or, conversely, acidic pH values, lead those skilled in the art to set aside or limit in practice the use of starches to the benefit of celluloses and/or synthetic polymers, which, nevertheless, have a higher cost price and are less biodegradable.

Moreover, during the manufacture of powders or granules for non-food and non-pharmaceutical use, it is preferred to select, if possible, supports and vector agents that have only very limited risks of explosability. These starches, like any finely divided powdered organic substance, are known to have risks of this nature, but under particular confinement conditions.

As a result, formulators occasionally have a tendency to set aside the use of starches and to prefer mineral substances such as silica, talc and calcium carbonate, although the performance qualities and functionalities of these products may be entirely different, or even mediocre and may thus necessitate the correction of these defects by using other substances that are generally expensive and nonbiodegradable.

It is seen from the foregoing that there is a need for a means that can be advantageously used in the general context of the preparation of non-food and non-pharmaceutical products and especially for a means that:

1) has a maximum of the abovementioned characteristics a) to j) and especially of the physical characteristics, a biodegradability and cost price that are suited to the current technical, economical and regulatory requirements, 2) is readily usable, without the need for expensive installations, on account of the risks of explosion that it might generate during its handling, 3) is usable for the maximum of functionalities desired in the field of manufacturing solid or liquid intermediate or finished products for non-food or non-pharmaceutical use, as finished product per se, for example in the form of paper-separating powders or adhesive powder or detergent or plant-protection granules, 4) is usable for the maximum number of active principles used in this field, and especially 5) is effective in media that may have pH values far from neutrality, in particular (very) alkaline pH values.

The Applicant Company has found that such a means can consist of a composition selected especially on the basis of 1) its presentation form, in the present case powdered or granular, and preferably in the case of granulation, a wet-granulated form, and 2) of its nature, by means of the mandatory presence of a legume starch and of an additive selected as a function of the non-food and non-pharmaceutical use intended for the composition.

More specifically, a subject of the invention is a powdered or granular composition, which is useful for preparing products for non-food and non-pharmaceutical use, characterized in that it contains:

at least one legume starch, having a) a starch content of greater than 90%, b) a protein content of less than 5% and c) an amylose content of greater than 20% and less than 60%, these percentages being expressed as dry weight relative to the total dry weight of said legume starch, and at least one additive chosen from a flow agent, a filler, a polymer and an active principle, or a mixture thereof.

Preferably:
a) the starch content is greater than 95% (dry/dry),
b) the protein content is less than 2% (dry/dry), and
c) the amylose content is between 22% and 55% (dry/dry).

Very advantageously, the legume starch is a pea starch having:
a) a starch content of greater than 98% (dry/dry),
b) a protein content of less than 1% (dry/dry), and
c) an amylose content of between 33% and 45% (dry/dry).

According to a first variant, the legume starches are native starches, of granular structure, of natural or hybrid origin, including those derived from genetic mutations or manipulations. They may be derived especially from bean, broad bean, horse bean, lentil or pea, including all of the respective varieties thereof.

According to another variant, the legume starches are products resulting from a chemical treatment, an enzymatic treatment and/or a physical treatment, in particular a thermal treatment, of a native starch, said treatment having the effect of conserving or not conserving the granular structure of the starting starch.

This definition especially includes crosslinked, esterified, etherified, oxidized, fluidized, pregelatinized, retrograded, enzyme-resistant and compacted starches of granular or nongranular structure, and mixtures thereof. These products ordinarily have a dextrose equivalent (DE) of less than 0.5.

The terms "granular starch" and "starch of granular structure" mean any native or modified starch for which the majority of the grains, i.e. at least 50% in numerical terms and up to 100% in numerical terms, show birefringence when observed by a microscope under polarized light.

According to a first advantageous mode, the legume starch is a native or modified granular starch, preferably from pea.

It may in particular be a granular starch that is native, i.e. not chemically, enzymatically or physically modified, in particular a native granular pea starch.

It may also be a granular starch, preferably from pea, which has been chemically, enzymatically and/or physically modified, for example by acidic, enzymatic or oxidative fluidization, by dextrinification, by esterification, by etherification, in particular by cationization, carboxyalkylation, ethoxylation or hydroxypropylation, by crosslinking, by microwave or ultrasound treatment, by atomization, by extrusion, by cooking or by heating, especially the operations known as "heat moisture treatment" or "annealing".

According to a second advantageous mode, the legume starch, preferably from pea, is a retrograded starch and/or is resistant to enzymes and in particular resistant to α-amylases, isoamylases or glucoamylases.

According to a third advantageous mode, the legume starch, preferably from pea, is a pregelatinized starch obtained in particular by performing a cooking-extrusion or a treatment on drying drums, so as to confer the starch a certain level of solubility in cold water, in contrast to granular starches.

The additive present in the composition in accordance with the invention is present therein in a content of between 1 and 9000 parts, preferably between 3 and 6000 parts, more preferably between 10 and 4000 parts per 10 000 parts of legume starch (dry/dry). It is selected from flow agents, fillers, polymers, active principles, alone or as a mixture.

The additive may be a flow agent. It is then preferably present in a content of between 1 and 200 parts per 10 000 parts (dry/dry) of legume starch; and is preferably selected from silicas, silicon oxides or aluminum oxides, calcium phosphates, calcium silicates, aluminosilicates, diatomaceous earths, talcs and kaolins.

The additive may also be a filler, preferably present in a content of between 50 and 9000 parts and more preferably between 100 and 6000 parts per 10 000 parts (dry/dry) of legume starch. It is advantageously selected from mineral fillers such as alkali metal and alkaline-earth metal carbonates, phosphates, sulfates and silicates, kaolins, micas, calcites, chalks, bentonites, clays, zeolites, talcs, aluminas, metal oxides, in particular zinc oxides, titanium oxides or silicon oxides, carbon blacks, mineral fibers, and from organic fillers such as alkali metal and alkaline-earth metal salts of organic acids, wood powders, cellulose-based powders and plant fibers. Advantageously, the filler used has a solubility in water of less than 5% and preferably 2%, and more preferably is insoluble in water.

The additive may also be a polymer, preferably present at between 10 and 6000 parts, more preferably between 100 and 4000 parts per 10 000 parts (dry/dry) of legume starch. It is preferably selected from polymers of synthetic origin such as polyvinyl alcohols, polyvinylpyrrolidones, (meth)acrylic acid (co)polymers and salts thereof, polyethylene glycols, polyesters, which are preferably biodegradable, for instance polylactates, polycaprolactones, polyesters of diacids (or polyacids) and of di(poly)alcohols and polymers of natural or fermentation origin such as xanthans, polyhydroxyalkanoates (PHA), starches, algal extracts, celluloses and proteins, and the respective derivatives thereof.

Finally, the additive may be an active principle preferably present at between 1 and 9000 parts and more preferably between 10 and 6000 parts per 10 000 parts (dry/dry) of legume starch. It is advantageously selected from surfactants such as wetting agents, antifoams, emulsifiers, detergents, degassing agents, lubricants and anti-adhesive agents, builders and cobuilders such as zeolites and polyacrylates, antifouling agents, antioxidants, color-transfer resistants, alkaline agents, oxidizing agents, dyes, pigments, bleaching activators, softeners, anticorrosion agents, biocides, pesticides, enzymes, bioactivators, plant-protection and veterinary active principles, vitamins, animal or plant nutrients, fertilizers, plasticizers such as urea, glycols, organic acid salts, sugar alcohols, for instance sorbitol, bonding agents and adhesives, fragrances, flame retardants, and any mixtures of at least any two of these products.

The present invention is also directed toward the use of a legume starch as defined above for the preparation of a powdered or granular composition for non-food and non-pharmaceutical use, said composition containing or being intended to contain at least one additive selected from a flow agent, a filler, a polymer, an active principle, or a mixture thereof.

Said use of the legume starch or of the composition according to the invention containing said legume starch may in particular be envisaged in the manufacture of detergent, plant-protection or absorbent powders, of adhesives, building materials, plastics or textiles, in particular and as will be illustrated later, as an antifoam support, as a tablet disintegrant, as an anti-smudge agent for offset printing and as an adhesive agent for plasterboards A subject of the present invention is in particular the use, in general terms, of a legume starch for the preparation of an anti-setoff agent for offset printing.

Other characteristics an advantages of the description will emerge clearly on reading the examples that follow, which are given as nonlimiting illustrations.

EXAMPLE 1

Antifoam Support

1. Formulation

| Support (native pea starch) | 10 000 | parts |
| Silicone oil HS DB 100 | 1467 | parts |
| POLYSORB ® 70/12/12 (binder) | 1075 | parts |
| Granulation water | 3472 | parts |

The pea starch has a starch content of greater than 98% (dry/dry), said starch having an amylose content of 35% (dry/dry pea starch) and a protein content of about 0.35% (dry/dry pea starch). The silicone oil is marketed by the company Dow under the name HS DB 100. The product Polysorb® 70/12/12 is a hydrogenated starch hydrolyzate marketed by the Applicant, with a solids content of about 70%.

2. Granulation

Equipment: Kenwood household mixer or equivalent equipped with a planetary moving arm, Erweka FGS wet granulator equipped with a 2500 μm grate, and Aeromatic fluidized dryer.

Procedure: introduce the starchy support and the binder into the Kenwood mixer. With stirring, successively incorporate the antifoam and then the water. After homogenization, pass the mixture obtained into the Erweka wet granulator. Dry on the fluidized-bed dryer at 40-50° C. to obtain a final moisture content in the region of 7%. Screen and retain the granulometric fraction of between 315 and 2500 μm.

3. Results

The tests were performed in comparison with corn starch and wheat starch.

| | Native starch of | | |
|---|---|---|---|
| | corn | wheat | pea |
| Granulometric distribution | | | |
| <315 μm | 28.7% | 6.7% | 16.7% |
| >315 μm | 71.3% | 93.3% | 83.3% |
| >2500 μm | 0.0% | 0.0% | 0.0% |
| Mean laser granulometry in μm | 489 CV = 65.9% | 1008 CV = 37.5% | 967 CV = 40.6% |
| Abrasion | 16% | 11% | 16% |
| Densities | | | |
| untamped | 0.60 | 0.64 | 0.56 |
| tamped | 0.64 | 0.68 | 0.62 |
| Moisture content | 7.15% | 6.4% | 7.0% |
| Stephansen whiteness | 53.2 | 74.4 | 65.1 |
| Antifoam effect % foam remaining | 19% | 18% | 16% |

4. Measurement of the Abrasion

Equipment: subject the particles to be tested to a mechanical action in a machine known as a friabilimeter (Erweka TA brand machine), the "abrasion drum" of which rotates at a spin speed of 25 rpm, and into which has been introduced one steel bead of about 17 mm in diameter and weighing about 19 g.

Procedure: introduce into the abrasion drum of this friabilimeter an amount of 15 g of product having a granulometry of between 315 and 2500 μm. Switch the machine on to spin for 5 minutes.

Results: at the end of the experiment, determine the weight proportion represented by the residue retained on a screen with a mesh size of 315 microns. The abrasion index corresponds to the percentage of powder not retained by the screen defined above. The abrasion is proportionately greater the higher the percentage of powder not retained by said screen.

5. Measurement of the Antifoam Effect

Equipment: a high-sided 2-liter glass beaker is used, placed in a bath thermostatically maintained at 40° C. The beaker is filled with 1 liter of drinking water at 40° TH and 40° C. containing 4 g of detergent. Stirring is performed using a 4-paddle stirrer (rotation: 1000 rpm) set such that its bottom edge is 35 mm from the base of the beaker.

Procedure: place in the 2-liter beaker 1 liter of drinking water at 40° TH/40° C. and 4 g of a detergent powder free of antifoam, to which is added 2% of the antifoam preparation to be evaluated relative to the detergent powder, and stir at 1000 rpm for 25 minutes. Stop the stirring every 5 minutes and record the supernatant foam height.

Results (determination of the % of remaining foam): the determination of the percentage of remaining foam is performed by calculating the average of the foam heights resulting from 5 repeated measurements and by calculating the percentage of remaining foam relative to the height of foam formed with a control test without antifoam.

EXAMPLE 2

Disintegrant/Detergent Tablets

1. Formulation Compositions

| | |
|---|---|
| Pea starch (permeabilizer) | 10 000 parts |
| Glycolys ® D (binder) | 1364 parts |
| Acusol ® 772 (swelling agent) | 2278 parts |
| Granulation water | 13 642 parts |

Glycolys ® D marketed by the Applicant
Acusol ® 772 marketed by the company Rohm & Haas.

2. Preparation of the Granules

Equipment: Kenwood household mixer or equivalent equipped with a planetary arm, Erweka FGS wet granulator equipped with a 1500 µm grate, and Aeromatic fluidized dryer.

Procedure: dry-mix the permeabilizer, the binder and the swelling agent in the Kenwood mixer. Incorporate the water with stirring. After homogenization, pass the mixture obtained into the Erweka wet granulator equipped with a 1500 µm grate. Dry on the fluidized-bed dryer at 40-50° C. to obtain a final moisture content of about 10%. Screen to obtain the desired granulometric fraction.

3. Preparation of the Tablets

Homogeneously mix a standard detergent powder and the granulated disintegrant to be tested. Place 40 g of the above mixture into a cylindrical tube with an inside diameter of 4 cm and a height of 10 cm, with a removable base to extract the tablet after compression. Place a sliding piston in the tube to allow the mixture to be compressed. Position the above system in a Perrier press and apply the desired pressure. For example, with a compact powder prepared in the laboratory, the force that needs to be applied is 2.5 kN, and with a commerical Skip micro powder, the force to be applied is only 1 kN.

4. Results

The pea starch having the composition mentioned in Example 1 is compared with native corn and wheat starches marketed by the Applicant.

| | Pea | Wheat | Corn |
|---|---|---|---|
| % Granulometric distribution of the granules | | | |
| 1600 to 850 µm | 0.95 | 1.10 | 1.00 |
| 850 to 630 µm | 1.95 | 4.20 | 6.00 |
| 630 to 200 µm | 35.10 | 26.40 | 21.60 |
| <200 µm | 62.00 | 68.30 | 71.40 |
| Density | | | |
| (i) untamped | 0.41 | 0.44 | 0.40 |
| (ii) tamped | 0.47 | 0.52 | 0.52 |
| Moisture content of the granules (%) | 9.50 | 11.65 | 8.70 |
| Whiteness | | | |
| (i) at 460 nm (barium sulfate = 98.3) | | | |
| Starch alone | 89.50 | 93.33 | 85.99 |
| Granules | 83.29 | 87.95 | 83.98 |
| (ii) Stephansen whiteness (barium sulfate = 97.55) | | | |
| Starch alone | 79.04 | 88.91 | 71.77 |
| Granules | 73.82 | 81.43 | 68.2 |
| Disintegration speed of the tablets with 200-630 µm granules | | | |
| SKIP ® micro/granules: 97%/3% | 46 | 54 | 50 |
| OMO ® micro/granules: 96%/4% | 58 | 70 | 64 |

The explosability characteristics of the native pea starches used for the preparation of the granulated disintegrants according to the invention and those of the native wheat and corn starches used for comparative purposes are given in the table below. These values were obtained by using the standardized methods in force.

| Starch | pea | wheat | corn |
|---|---|---|---|
| Minimum ignition energy (mJ) | 1200 | 45 | 225 |
| KST (bar m/s) | 73 | 120 | 124 |
| Max. explosion pressure (bar) | 6.6 | 8 | 8.5 |
| T° of self-ignition in cloud (° C.) | 460 | 460 | 480 |

Measurement of the Disintegration Speed of the Tablets

Principle: to perform this test, the tablet to be tested is placed in the water inlet tray of a Bosch top-loading washing machine. The washing machine is fed by a pump connected to a water tank. Consequently, the amount of water may optionally be modified and the water inlet pressure in the washing machine is constant.

Result: the disintegration speed in seconds is measured from the time at which the inlet water starts, up to the total disintegration of the tablet.

EXAMPLE 3

Anti-Setoff Agent for Offset Printing

1. Formulation

Mixtures (native and granular starch or potato starch-flow agent) were prepared using a mixer of food processor type (mixing time of 30 seconds).

Various flow agents were used:

Aerosil® RL972 precipitated amorphous silica,

Neosyl® GP amorphous synthetic silicon dioxide,

Microcal® ET, precipitated amorphous synthetic calcium silicate hydrate,

Alusyl® ET, precipitated amorphous alumino-silicate hydrate, tricalcium phosphate.

2. Results

A pea starch, similar to that of Example 1, is compared with the granular corn starch Fluidamid® A, native potato starch (marketed by the Applicant) and a mixture of 50% native corn starch/50% native potato starch.

| Starch or potato starch (10.000 p.) | Mean particle diameter | Appearance | Density tamped | Density untamped | Powder cone height (cm) | Dusting (s) |
|---|---|---|---|---|---|---|
| Pea | 27.9 μm | white | 0.794 | 0.642 | 2.5 | 6 |
| Pea + 5 p. Aerosil ® | 27.9 μm | white | 0.926 | 0.763 | 1.3 | 7 |
| Pea + 5 p. Neosyl ® GP | 27.9 μm | white | 0.894 | 0.726 | 1.5 | 7 |
| Pea + 10 p. Microcal ® | 27.9 μm | white | 0.842 | 0.684 | 1.8 | 8 |
| Pea + 10 p. Alusyl ® | 27.9 μm | white | 0.884 | 0.736 | 1.6 | 7 |
| Pea + 50 p. $Ca_2(PO_4)_3$ | 27.9 μm | white | 0.900 | 0.757 | 0.9 | 5 |
| potato starch | 40.1 μm | white | nd | nd | 0.9 | 15 |
| Corn/potato starch | 33.2 μm | beige | nd | nd | 0.8 | 18 |
| Fluidamid ® A | 19.3 μm | beige | 1.000 | 0.837 | 0.8 | 20 |

3. Measurement of the Height of a Cone of Powder

Equipment: cylinder 50 mm in diameter and 5 mm wide, fixed on a foot such that the upper edge of the metal disc is 80 mm in height, 500 μm metal screen, steel ruler graduated in mm.

Procedure: place the 500 μm screen 10 cm above the top of the cylinder. Sprinkle the powder through the screen to make it "fall like snow". Continue this operation until a pointed cone forms on the cylinder and the height of this cone has stabilized (it may be necessary to repeat this operation several times if the cone collapses). Measure the height of the cone using the steel ruler.

Results: the results correspond to the arithmetic mean of two measurements of the cone height, expressed in cm.

4. Measurement of the Dusting 25 g of anti-smudge powder are introduced into a 2-liter closed glass jar. The jar is upturned 5 times in succession and then stood on a work surface. The time required for all of the dust in suspension to fall down is recorded. The results, in seconds, correspond to the average of the values obtained for 2 measurements.

EXAMPLE 4

Adhesive Agent/Plasterboards

1. Formulation

The adhesive power of various modified granular pea starches is evaluated in the manufacture of plasterboards, in comparison with the fluidized corn starch Fluitex® 065X (control) marketed by the Applicant in this application.

The pea starches evaluated are the following:
acetylated fluidized pea starch with an acetyl index of 2.3% and a water content of 12%, supplemented with 30 parts by weight of precipitated amorphous silica Aerosil® RL972 per 10 000 parts of pea starch (Starch 1),
acetylated fluidized pea starch with an acetyl index of 1.6% and a water content of 12.1%, supplemented with 30 parts of precipitated amorphous silica Aerosil® RL972 per 10 000 parts of pea starch (Starch 2),
pea starch oxidized with bleach obtained by treating at about 30° C. a pea starch milk containing 34% solids, 33% vol./com. of bleach (chlorometric degree: 47°, pH regulated to 9.5), and then by leaving in contact until the bleach is depleted and, finally, neutralizing, filtering off and drying the oxidized starch thus obtained. 30 parts by weight of precipitated amorphous silica Aerosil® RL972 are added to this starch per 10 000 parts of pea starch (Starch 3),
pea starch having the composition mentioned in Example 1 and used as starting material in the manufacture of Starches 1 to 3 above, also supplemented with 30 parts by weight of precipitated amorphous silica Aerosil® RL972 per 10 000 parts of pea starch (Starch 4).

Starches 1 to 4 and the Control are used in the manufacture of plasterboards according to a given and constant manufacturing protocol. The adhesive power is evaluated by means of a peel test on the constituent cardboards (recto and verso faces) of the plasterboard. The control is made.

2. Results

|  | Peel test | |
|---|---|---|
|  | Recto | Verso |
| Control | 20 | 20 |
| Starch 1 | 20 | 20 |
| Starch 2 | 18 | 18 |
| Starch 3 | 20 | 20 |
| Starch 4 | 0 | 0 |

0: absence of bonding
20: excellent bonding

3. Peel Measurement

Equipment: a 1 l plastic pot, a 2 l stainless-steel puddling bowl, 3 ovens, one of which is saturated with water, a 7.5 cm×15 cm rectangular springform mold, a 10 kg weight, and two 7.5 cm×9 cm PVC plates.

Procedure: cut the cardboards (of the type used for plasterboards) to dimensions of 7.5 cm×15 cm. Mix 300 g of plasterboard plaster with 1.5 g of accelerator (dried ground tile) and the amount of starchy material to be tested in the 1 l plastic pot. Weigh 210 g of drinking water at 20° C. in the puddling bowl and then introduce the powder mixture. Puddle vigorously for 45 seconds. Pour the puddled mixture into the mold, at the base of which has been placed beforehand a sheet of plasterboard cardboard (Kraft face upwards), and then cover the top of the mold with a second sheet of cardboard (Kraft face downwards). Place the 2 PVC plates on the cardboard so as to cover the mold. Place the 10 kg weight on the two plates. Wait for 10 minutes before removing the weight and taking the board out of the mold. Leave the board to stand in the open for 10 minutes. Place the board vertically in the first water-saturated oven set at 180° C. for 20 minutes, and then in a second ventilated oven at 110° C. for 20 minutes and finally in a third ventilated oven at 45° C. for 24 hours. Recondition the board obtained for 24 hours at 20° C. and 65% RH. Using a cutter, mark 2 diagonal notches on each face of the board. Evaluate the bonding by peeling off the paper, starting from the center and drawing in the 4 opposite directions.

The invention claimed is:

1. A powdered or granular composition, which is useful for preparing products for non-food and non-pharmaceutical use, wherein said composition contains:
at least one native granular legume starch having:
a) a starch content of greater than 90%,
b) a protein content of less than 5%,
c) an amylose content of greater than 20% and less than 60%, these percentages being expressed as dry weight relative to the total dry weight of said legume starch, and at least one additive selected from a flow agent, a filler, a polymer, an active principle, or a mixture thereof.

2. The composition as claimed in claim 1, wherein the legume starch has:
   a) a starch content of greater than 95% (dry/dry),
   b) a protein content of less than 2%, and
   c) an amylose content of between 22% and 55% (dry/dry).

3. The composition as claimed in claim 2, wherein the legume starch is a pea starch having:
   a) a starch content of greater than 98% (dry/dry),
   b) a protein content of less than 1%, and
   c) an amylose content of between 33% and 45% (dry/dry).

4. The composition as claimed in claim 1, wherein the legume starch has a total content of constituents other than starch and proteins of less than 5% (dry/dry).

5. The composition as claimed in claim 1, wherein the additive content is between 1 and 9000 parts, per 10 000 parts of legume starch (dry/dry).

6. The composition as claimed in claim 1, wherein the additive content is between 3 and 6000 parts, per 10 000 parts of legume starch (dry/dry).

7. The composition as claimed in claim 1, wherein the additive content is between 10 and 4000 parts per 10 000 parts of legume starch (dry/dry).

8. The composition as claimed in claim 1, wherein the additive is a flow agent.

9. The composition as claimed in claim 1, wherein the flow agent is present in a content of between 1 and 200 parts, per 10 000 parts of legume starch (dry/dry).

10. The composition as claimed in claim 1, wherein the additive is a filler.

11. The composition as claimed in claim 10, wherein the filler, is present in a content of between 50 and 9000 parts, per 10 000 parts of legume starch (dry/dry).

12. The composition as claimed in claim 10, wherein the filler is present in a content of between 100 and 6000 parts, per 10 000 parts of legume starch (dry/dry).

13. The composition as claimed in claim 1, wherein the additive is a polymer.

14. The composition as claimed in claim 13, wherein the polymer is present in a content of between 10 and 6000 parts, per 10 000 parts of legume starch (dry/dry).

15. The composition as claimed in claim 13, wherein the polymer is present in a content of between 100 and 4000 parts, per 10 000 parts of legume starch (dry/dry).

16. The composition as claimed in claim 1, wherein the additive is an active principle.

17. The composition as claimed in claim 16, wherein the active principle is present in a content of between 1 and 9000 parts, per 10 000 parts of legume starch (dry/dry).

18. The composition as claimed in claim 16, wherein the active principle is present in a content of between 10 and 6000 parts, per 10 000 parts of legume starch (dry/dry).

19. A powdered or granular composition, which is useful for preparing products for non-food and non-pharmaceutical use, wherein said composition contains:
   at least one native granular legume starch having:
   a) a starch content of greater than 90%,
   b) a protein content of less than 5%,
   c) an amylose content of greater than 20% and less than 60%,
   these percentages being expressed as dry weight relative to the total dry weight of said legume starch, and
   at least one additive selected from a flow agent, a filler, a polymer, an active principle, or a mixture thereof,
   wherein said composition is an antifoam support, a tablet disintegrant, or an anti-setoff agent for offset printing.

20. Process for the manufacture of a detergent, plant-protection or absorbent powders, of adhesives, of building materials, of plastics or textiles, wherein said process comprises:
   providing at least one native granular legume starch having:
   a) a starch content of greater than 90%,
   b) a protein content of less than 5%,
   c) an amylose content of greater than 20% and less than 60%,
   these percentages being expressed as dry weight relative to the total dry weight of said legume starch;
   providing at least one additive selected from a flow agent, a filler, a polymer, an active principle, or a mixture thereof;
   at least one step of physical mixing or at least one step of granulation, especially wet granulation, of the legume starch(es) and the additive(s),
   wherein said step of physical mixing or granulation is moreover optionally preceded or followed by at least one step selected from the group comprising hydration, drying, compacting, pelletization, densification, grinding, screening, spheronization, coating, film-coating and hard-coating treatments.

21. An anti-setoff agent for offset printing comprising at least one native granular legume starch having:
   a) a starch content of greater than 90%,
   b) a protein content of less than 5%,
   c) an amylase content of greater than 25% and less than 60%,
   these percentages being expressed as dry weight relative to the total dry weight of said legume starch.

22. The composition as claimed in claim 2, wherein the legume starch has a total content of constituents other than starch and proteins of less than 5% (dry/dry).

23. The composition as claimed in claim 3, wherein the legume starch has a total content of constituents other than starch and proteins of less than 5% (dry/dry).

* * * * *